United States Patent [19]

Huang et al.

[11] Patent Number: 4,772,732

[45] Date of Patent: Sep. 20, 1988

[54] METHOD FOR PURIFICATION OF BUTYLENE OXIDE

[75] Inventors: Mao Y. Huang, Riverview; Lawrence E. James, Grosse Ile; Joseph F. Louvar, Lincoln Park, all of Mich.; Ernst Langer, Ellerstadt, Fed. Rep. of Germany

[73] Assignees: BASF Corporation, Parsippany, N.J.

[21] Appl. No.: 860,842

[22] Filed: May 8, 1986

[51] Int. Cl.$^4$ ............................................. C07D 301/32
[52] U.S. Cl. ..................................................... 549/542
[58] Field of Search ......................................... 549/542

[56] References Cited

U.S. PATENT DOCUMENTS

| 2,706,189 | 4/1955 | Pruitt et al. | 549/542 |
| 2,993,916 | 7/1961 | Normington | 549/542 |
| 3,022,259 | 2/1962 | Pearce | 549/542 |

FOREIGN PATENT DOCUMENTS

| 767172 | 6/1971 | Belgium | 549/542 |
| 186522 | 9/1985 | Japan | 549/541 |

OTHER PUBLICATIONS

B. D. Pearson et al., Chemistry and Industry, Feb. 26, 1966, p. 370.

*Primary Examiner*—Norma S. Milestone
*Attorney, Agent, or Firm*—Bill C. Panagos;

[57] ABSTRACT

The invention discloses a method for purifying butylene oxide by using an anion exchange resin and an adsorbent. The anion exchange resin removes acid and aldehyde impurities while the adsorbent removes water impurities from the butylene oxide. Depending upon the impurity level, the purification steps can be conducted singularly or in combination, and the process can proceed either batchwise in a reactor or continuously in a column. The ion exchange resin of the choice is a sulfonated macroreticular anion exchange resin and the adsorbent of choice is a molecular sieve.

6 Claims, No Drawings

METHOD FOR PURIFICATION OF BUTYLENE OXIDE

BACKGROUND OF THE INVENTION

1. Field of Invention

Butylene oxide is used in a number of commercial applications. Any impurities in the butylene oxide interfere with use of the butylene oxide in subsequent reactions resulting in a lower grade product. Conventional methods of purification of butylene oxide are too costly once the butylene oxide is shipped from the manufacturing site.

It is an object of this invention to disclose a process for purifying butylene oxide which is economical and commercially feasible. In particular, the process is practicable at a location other than the butylene oxide manufacturing site. It is a further object to reduce the impurity level of butyric acid and butyraldehyde in butylene oxide. It is a further object to provide a process for removing impurities with a material which can be regenerated easily and reused.

These and other objects which will become apparent to those skilled in the art are accomplished by the process of the invention.

2. Description of Prior Art

The use of ion exchange resins for purification purposes are well known in the art. In particular, use of nonaqueous macroreticular sulfonated anion exchange resins is well known. Also disclosed in the art is use of molecular sieves as adsorbents.

SUMMARY OF THE INVENTION

The invention discloses a method for purifying butylene oxide by using an anion exchange resin and an adsorbent. The anion exchange resin removes acid and aldehyde while the adsorbent removes water impurities from the butylene oxide. Depending upon the impurity level, the purification steps can be conducted singularly or in combination, and the process can proceed either batchwise in a reactor or continuously in a column. The anion exchange resin of choice is a sulfonated macroreticular anion exchange resin and the adsorbent of choice is a molecular sieve.

DESCRIPTION OF THE PREFERRED EMBODIMENT

Typical product specifications for butylene oxide are in the range of 25 ppm to 100 ppm butyric acid, 100 ppm to 500 ppm butyraldehyde, and 500 ppm to 2500 ppm water. However, for certain applications a higher grade of butylene oxide is desired. The level of impurities in butylene oxide may also increase if exposed to air or moisture as a result of improper storage. Repurifying quantities of bulk butylene oxide once the butylene oxide has been shipped from the manufacturing plant thus becomes necessary. The conventional method of purifying butylene oxide is via distillation. However, setting up a distillation operation for such a purpose is not an economical option once the butylene oxide has been shipped from the manufacturing site.

The subject invention discloses a method of purifying butylene oxide using anion exchange resins and adsorbents. Anion exchange resins can effectively remove acid and aldehyde impurities while adsorbents can effectively remove water.

In the process of the invention, butylene oxide is contacted with an anion exchange resin to remove acid and aldehyde impurities. Subsequently, butylene oxide is contacted with adsorbents such as molecular sieves and activated alumina to remove water. Both treatments can be conducted singly or in combination. Additionally, the contacting process can be carried out batchwise, in a reactor, or continuously in a column. The following describes the two alternative methods.

1. Batch Operation:

Butylene oxide is charged into a vessel. Reagents, and activated anion exchange resins or adsorbents, are added at a fraction of butylene oxide weight. The mixture is well agitated until equilibrium is attained. The mixture is then filtered to remove solid reagents. The treatment is repeated until the desired purity level is achieved.

2. Continuous Operation:

A purification process is set up in series. The process proceeds in the following sequence:
  (1) passing butylene oxide through the anion exchange column,
  (2) passing butylene oxide through the adsorbent column,
  (3) neutralizing the columns with dilute caustic solution,
  (4) washing the columns with water,
  (5) purging the anion exchange column with nitrogen,
  (6) drying the adsorbent column with hot nitrogen,
  (7) washing the columns with methanol,
  (8) vacuum drying the anion exchange column,
  (9) drying the adsorbent column with hot nitrogen.

The following examples are presented for illustration of the process of the invention and the results obtained thereof.

EXAMPLE 1

One hundred grams of butylene oxide containing 185 ppm butyric acid and 360 ppm butyraldehyde was mixed with 1 gram of Amberlyst®A21, Amberlyst®A26, and Amberlyst®A27 anion exchange resins, respectively, at room temperature for 22 hours. After filtering out the resins, the treated butylene oxide was found to have the following impurity levels.

| Reagent | Butyric Acid | Butyraldehyde |
|---|---|---|
| Amberlyst ® A-21 | 6 ppm | 220 ppm |
| Amberlyst ® A-26 | 0 ppm | 100 ppm |
| Amberlyst ® A-27 | 2 ppm | 140 ppm |
| None | 185 ppm | 360 ppm |

"Amberlyst" is a registered trademark of the Rohm and Haas Company for a macroreticular sulfonate anion exchange resin.

The impurity level was largely reduced.

EXAMPLE 2

Two hundred fifty grams of butylene oxide containing 127 ppm butyric acid, 550 ppm butyraldehyde, and 740 ppm water was mixed with 7.5 grams of molecular sieve and 7.2 grams of activated alumina, respectively, at room temperature for three hours. After filtering out the adsorbents, the treated butylene oxide was found to have the following impurity levels:

| Reagent | Butyric Acid | Butyraldehyde | Water |
|---|---|---|---|
| Molecular sieve | 58 ppm | 460 ppm | 520 ppm |

-continued

| Reagent | Butyric Acid | Butyraldehyde | Water |
|---|---|---|---|
| Activated alum | 45 ppm | 400 ppm | 490 ppm |
| None | 127 ppmp | 550 ppm | 740 ppm |

After three hours of contact time the water level was greatly reduced.

The embodiments of the invention in which an exclusive property or privilege is claimed are defined as follows:

1. A process for removing butyraldehyde, butyric acid and water impurities from butylene oxide comprising contacting said butylene oxide with a macroreticular sulfonate anion exchange resin and an adsorbent selected from the group consisting of a molecular sieve and activated alumina, and removing said adsorbent and anion exchange resin from said purified butylene oxide.

2. The process of claim 1 wherein said anion exchange resin is a non-aqueous macroreticular sulfonate anion exchange resin and said adsorbent is a molecular sieve.

3. The process of claim 1 wherein removing said impurities by contacting butylene oxide with said resin and said adsorbent is conducted sequentially.

4. The process of claim 1 wherein removing said impurities by contacting butylene oxide with said resin and said adsorbent is conducted in a one-step process.

5. The process of claim 1 wherein removing said impurities by contacting butylene oxide with said resin and said adsorbent is conducted batchwise in a reactor.

6. A process for removing butyraldehyde, butyric acid and water impurities to obtain a purified butylene oxide sequentially contacting the butylene oxide with a macroreticular sulfonate anion exchange resin and an adsorbent selected from the group consisting of a molecular sieve or activated alumina continuously in a column.

* * * * *